US009285298B2

(12) United States Patent
Takegawa et al.

(10) Patent No.: US 9,285,298 B2
(45) Date of Patent: Mar. 15, 2016

(54) METHOD OF ANALYZING MICROPARTICLE COMPOSITION AND MICROPARTICLE COMPOSITION ANALYZING DEVICE

(75) Inventors: Nobuyuki Takegawa, Tokyo (JP); Takayuki Nakamura, Tokyo (JP); Yuuki Sameshima, Tokyo (JP); Masahiko Takei, Tokyo (JP); Noritomo Hirayama, Tokyo (JP)

(73) Assignees: THE UNIVERSITY OF TOKYO, Tokyo (JP); FUJI ELECTRIC CO., LTD., Kanagawa (JP)

( * ) Notice: Subject to any disclaimer, the term of this patent is extended or adjusted under 35 U.S.C. 154(b) by 692 days.

(21) Appl. No.: 13/635,304

(22) PCT Filed: Dec. 6, 2010

(86) PCT No.: PCT/JP2010/071818
§ 371 (c)(1),
(2), (4) Date: Sep. 14, 2012

(87) PCT Pub. No.: WO2011/114587
PCT Pub. Date: Sep. 22, 2011

(65) Prior Publication Data

US 2013/0011930 A1 Jan. 10, 2013

(30) Foreign Application Priority Data

Mar. 17, 2010 (JP) ................................ 2010-060467

(51) Int. Cl.
*G01N 24/00* (2006.01)
*G01N 1/22* (2006.01)
(Continued)

(52) U.S. Cl.
CPC ........... *G01N 1/2202* (2013.01); *G01N 1/4077* (2013.01); *G01N 1/2205* (2013.01);
(Continued)

(58) Field of Classification Search
CPC ............. C01P 2004/64; C01P 2004/04; C01P 2004/51; C01P 2004/62; C01P 2004/80; C01P 2004/02; C01P 2004/03; C01P 2004/60; C01P 2004/61; C01P 2006/10; A61F 13/53; A61F 2002/016; A61F 2230/0091
See application file for complete search history.

(56) References Cited

U.S. PATENT DOCUMENTS 4,383,171 A 5/1983 Sinha et al.
5,270,542 A 12/1993 McMurry et al.
(Continued)

FOREIGN PATENT DOCUMENTS

CN 1599635 A 3/2005
JP 07505218 A 6/1995
(Continued)

OTHER PUBLICATIONS

Woolfenden and McClenny, "Compendium of Methods for the Determination of Toxic Organic Compounds in Ambient Air Second Edition Compendium Method TO-17 Determination of Volatile Organic Compounds in Ambient Air Using Active Sampling Onto Sorbent Tubes", Center for Environm. Res. Inform. , EPA, 1999.*
(Continued)

*Primary Examiner* — Yelena G Gakh
(74) *Attorney, Agent, or Firm* — Holtz, Holtz & Volek PC

(57) ABSTRACT

A method of analyzing microparticle compositions and a microparticle composition analyzing device are capable of quantitatively analyzing the mass concentration of air microparticles online for each chemical composition. The particle ray of microparticles in an air sample is converged, and is irradiated onto a narrow domain of a capture body which includes a mesh-shaped structure for capturing the microparticles in the particle ray while removing surplus gas phase components, and the microparticles are captured. Then, the narrow region is subjected to concentrated irradiation of energy rays, and the microparticles that are captured by the capture body are vaporized, sublimated or reacted to yield a desorbed component, which is analyzed.

12 Claims, 16 Drawing Sheets

(51) Int. Cl.
*G01N 1/40* (2006.01)
*G01N 15/00* (2006.01)

(52) U.S. Cl.
CPC ...... *G01N1/2208* (2013.01); *G01N 2001/2223* (2013.01); *G01N 2015/0046* (2013.01); *Y10T 436/24* (2015.01)

(56) References Cited

U.S. PATENT DOCUMENTS

| | | | |
|---|---|---|---|
| 6,040,574 | A | 3/2000 | Jayne et al. |
| 7,311,751 | B2 | 12/2007 | Mei et al. |

FOREIGN PATENT DOCUMENTS

| | | | |
|---|---|---|---|
| JP | 2000180316 | A | 6/2000 |
| JP | 2001511257 | A | 8/2001 |
| JP | 2001351569 | A | 12/2001 |
| JP | 2002506201 | A | 2/2002 |
| JP | 2004028741 | A | 1/2004 |
| JP | 2007309878 | A | 11/2007 |
| WO | 03047720 | A1 | 6/2003 |

OTHER PUBLICATIONS

Wong et al., "Effects of Catalytic Wire-mesh Traps on the Level and Measurement of Heavy-Duty Diesel Particulate Emissions", SAE Technical Paper 840172, 1984, pp. 97-107.*
Chinese Office Action dated Sep. 16, 2014, issued in counterpart Chinese Application No. 201080065448.1.
International Search Report dated Mar. 8, 2011 issued in International Appln. No. PCT/JP2011/071818.
Herbert J. Tobias et al; Chemical Analysis of Diesel Engine Nanoparticles Using a Nano-DMA/Thermal Desorption Particle Beam Mass Spectrometer; Environmental Science & Technology; 2001; pp. 2233-2243.
John J. Jayne et al; Development of an Aerosol Mass Spectrometer for Size and Composition Analysis of Submicron Particles; Aerosol Science & Technology; 2000, pp. 49-70.
JD Allan et al; Quantitative Sampling Using an Aerodyne Aerosol Mass Spectrometer 1 ;J. Geophy Res; 2003; vol. 108.
JD Allan et al; Quantitative Sampling Using an Aerodyne Aerosol Mass Spectrometer 2; J. Geophy Res; 2003; vol. 108.

* cited by examiner

45

METHOD OF ANALYZING MICROPARTICLE COMPOSITION AND MICROPARTICLE COMPOSITION ANALYZING DEVICE

This application is a U.S. National Phase Application under 35 USC 371 of International Application PCT/JP2010/071818 filed Dec. 6, 2010.

TECHNICAL FIELD

The present invention relates to a method of analyzing a microparticle composition and an apparatus for analyzing a microparticle composition, which are suitable for quantifying, for example, a mass concentration of each chemical composition of microparticles floating in air (aerosol).

BACKGROUND ART

In recent years, there is a growing concern about an influence of an atmospheric environment on health, and for example, a new environmental standard for an atmospheric microparticle concentration has been established. For example, diesel microparticles are deposited in the back of the airway such as the alveoli to harm health. A particle size of microparticles is an important factor for a health risk. As the particle size is smaller, there is a higher risk that the particles reach the alveoli through the mouth, nose, trachea, and bronchi that are organs of respiration of a human to harm health. Thus, a standard based on an atmospheric concentration of particles (PM2.5) having an aerodynamic diameter of 2.5 μm or the like is also known. Further, in a special environment in which higher cleanliness of an atmospheric environment is required, such as a clean room, a production environment, or a medical environment, there is a demand for a method of measuring an atmospheric microparticle concentration with higher sensitivity.

In order to avoid a health influence risk and reduce a risk of deterioration in quality of products and services using a special atmospheric environment such as a clean room, a production environment, or a medical environment, it is important to monitor the status of a concentration of contamination with atmospheric microparticles. Further, it is important to obtain information on a mass concentration of each chemical composition of atmospheric microparticles, in order to identify a source of contamination to improve an atmospheric environment.

Conventionally, as a method of measuring a chemical composition of atmospheric microparticles, a filter collection and offline chemical analysis method has been widely used. This method involves sucking air to collect microparticles on a filter, transferring the microparticles to an analysis chamber or the like, followed by solution extraction, heat treatment, or the like, and chemically analyzing the microparticles. However, according to this method, it takes a collection time of about several hours to several days for analyzing an average atmospheric environment concentration level. A highly volatile component may be evaporated while being collected and transferred, and a gas phase component may adsorb to serve as an interfering factor during the collection of the microparticles. Thus, the above-mentioned method has a problem in terms of quantitativity. Further, the method is performed by offline analysis, and hence, it requires a great amount of labor for obtaining data continuously for a long period of time.

Accordingly, there is a demand for the development of a method for online measurement of a chemical composition, characteristics, and the like of atmospheric microparticles. As an apparatus and method applicable to such online measurement, for example, Patent Literature 1 below describes a method involving introducing particles into a high-vacuum chamber, irradiating flying particles with a laser to ionize a constituent component thereof, and analyzing a mass of the ionized component. Further, Patent Literature 2 and Non Patent Literatures 1 and 2 below describe a method involving introducing a particle beam generated by a particle beam generator (aerodynamic lens) for generating a particle beam of microparticles in a gas into a high-vacuum chamber, causing the particles to collide with a heated copper substrate with a molybdenum foil formed on the surface, heated tungsten, or the like to heat and gasify the particles, ionizing the resultant particles, and analyzing a mass of the particles.

CITATION LIST

Patent Literature

[PTL 1] U.S. Pat. No. 4,383,171 A

[PTL 2] U.S. Pat. No. 6,040,574 A

Non Patent Literature

[NPL 1] HERBERT J. TOBIAS and eight others, "Chemical Analysis of Diesel Engine Nanoparticles Using a Nano-DMA/Thermal Desorption Particle Beam Mass Spectrometer," 2001, ENVIRONMENTAL SCIENCE & TECHNOLOGY, 35 (11), p. 2233-2243

[NPL 2] John T. Jayne and seven others, "Development of an Aerosol Mass Spectrometer for Size and Composition Analysis of Submicron Particles," 2000, Aerosol Science and Technology, 33, p. 49-70

SUMMARY OF INVENTION

Technical Problem

However, according to the method described in Patent Literature 1, for example, microparticles to be irradiated with a laser having an intensity required for ionizing a constituent component of flying particles are only a part of the entire particles, and a difference in physical properties of the particles largely influence an ionization efficiency. Therefore, the method can only be applied to qualitative analysis and cannot be applied to quantitative analysis. Further, according to the methods described in Patent Literature 2 and Non Patent Literatures 1 and 2, a particle beam of microparticles to be introduced into vacuum has a speed of tens to hundreds of meters per second for example. When microparticles constructed of a partial mineral salt, soot, a partial organic substance, and the like collide with a substrate or the like placed for heating and gasification, most or all of the microparticles are bounced back and cannot be heated and gasified. Therefore, only qualitative analysis is applied to such microparticles, and quantitative analysis cannot be applied thereto.

Thus, it is an object of the present invention to provide a method of analyzing a microparticle composition and an apparatus for analyzing a microparticle composition, which allow online quantitative analysis of a mass concentration of each chemical composition of atmospheric microparticles.

Solution to Problem

The inventors of the present invention have made extensive studies in order to achieve the object. As a result, the inventors have found that, through the use of a particle trap having a mesh-shaped structure, atmospheric microparticles from a particle beam of the microparticles generated by a particle beam generator (aerodynamic lens) can be efficiently condensed and captured in a relatively narrow region, and further, the captured microparticles are irradiated with an energy beam to yield a desorbed component to be analyzed efficiently, and the desorbed component can be introduced into an analysis unit. Thus, the present invention has been completed.

That is, a method of analyzing a microparticle composition of the present invention includes: converging a particle beam of microparticles in a gas sample having removed therefrom an excess gas phase component; capturing the microparticles by a particle trap, which has a mesh-shaped structure for capturing the microparticles in the particle beam, through irradiation of a narrow region of the particle trap with the particle beam; vaporizing, sublimating, or reacting the microparticles captured by the particle trap through concentrated irradiation of the narrow region with an energy beam to yield a desorbed component; and analyzing the desorbed component.

According to the method of analyzing a microparticle composition of the present invention, a particle beam of microparticles in a gas sample is converged, having removed therefrom an excess gas phase component, and further a particle trap having a mesh-shaped structure is irradiated with the particle beam of microparticles in the gas sample to capture the microparticles. Therefore, atmospheric microparticles can be efficiently condensed and captured in a relatively narrow space region. Then, the particle trap is irradiated with an energy beam to vaporize, sublimate, or react the microparticles captured by the particle trap, thereby yielding a desorbed component. Therefore, energy can be concentrated to the captured atmospheric microparticles, and a desorbed component of a high concentration can be yielded in a short period of time and analyzed. This allows the online quantitative analysis of a mass concentration of each chemical composition of atmospheric microparticles. Meanwhile, when the particle trap is irradiated with an energy beam, the atmospheric microparticles captured by the particle trap are desorbed in a short period of time, and the particle trap becomes ready to capture the subsequent microparticles. Therefore, online measurement can be performed with a high time resolution (several minutes to one hour) even with respect to an average atmospheric environment concentration level.

Further, the present invention can handle microparticles with various chemical compositions by selecting or controlling the energy beam depending upon energy absorption characteristics of constituent components of the microparticles.

Further, when the microparticles are captured by the particle trap, a highly volatile component can be captured and analyzed by controlling a temperature of the particle trap to a temperature at which evaporation of a highly volatile component of the microparticles captured by the particle trap is reduced.

Further, the desorbed component is converted into another substance through the use of a catalyst, and the converted substance is analyzed, whereby, for example, a plurality of kinds of carbon compounds which are desorbed from an organic substance by heating are all oxidized to be converted into carbon dioxide, and the organic substance can be detected intensively and efficiently.

In the method of analyzing a microparticle composition of the present invention, it is preferred that the mesh-shaped structure be formed of a noble metal having a catalytic action. With this, the particle trap has a capturing action of capturing atmospheric microparticles efficiently and also has a catalytic action of converting the desorbed component into a form to be subjected to analysis.

In the method of analyzing a microparticle composition of the present invention, it is preferred that the mesh-shaped structure include a first mesh-shaped structure having a predetermined porosity, which is placed on a front surface side to be irradiated with the particle beam, and a second mesh-shaped structure having a porosity smaller than that of the first mesh-shaped structure, which is placed on an opposite surface side to the side to be irradiated with the particle beam, the opposite surface side being connected to the first mesh-shaped structure. With this, microparticles having once entered a mesh-shaped structure can be captured by the first mesh-shaped structure, microparticles having passed through the first mesh-shaped structure can be captured by the second mesh-shaped structure, and microparticles having passed through the first mesh-shaped structure and having been bounced back by the second mesh-shaped structure can be captured by the first mesh-shaped structure. Thus, the microparticles can be prevented from flowing out and atmospheric microparticles can be captured efficiently.

In the method of analyzing a microparticle composition of the present invention, it is preferred that the mesh-shaped structure include a first mesh-shaped structure having a predetermined porosity, which is placed on a front side of the particle trap which is a side which is to be irradiated with the particle beam, and a second mesh-shaped structure having a porosity smaller than that of the first mesh-shaped structure, which is placed on an opposite side (back side) of the particle trap which is a side opposite to the front side to be irradiated with the particle beam, the second mesh-shaped structure being connected to the first mesh-shaped structure. With this, microparticles having once entered a mesh-shaped structure can be captured by the first mesh-shaped structure, microparticles having passed through the first mesh-shaped structure can be captured by the second mesh-shaped structure, and microparticles having passed through the first mesh-shaped structure and having been bounced back by the second mesh-shaped structure can be captured by the first mesh-shaped structure. Thus, the microparticles can be prevented from flowing out and atmospheric microparticles can be captured efficiently.

In the method of analyzing a microparticle composition of the present invention, it is preferred that the mesh-shaped structure include a front-side mesh-shaped structure having a predetermined porosity, which is placed on a front side of the particle trap which is a side which is to be irradiated with the particle beam, and a plate having no void, which is placed on an opposite side (back side) of the particle trap which is a side opposite to the front side to be irradiated with the particle beam, the plate being connected to the front-side mesh-shaped structure. With this, microparticles having once passed through the front-side mesh-shaped structure and having been bounced back by the plate can be captured by the front-side mesh-shaped structure. Thus, the microparticles can be prevented from flowing out and atmospheric microparticles can be captured efficiently.

According to the apparatus for analyzing a microparticle composition of the present invention, the particle beam generator forms a particle beam in which microparticles in gas are condensed in a beam shape, an excess gas phase component is removed, and the particle trap having a mesh-shaped structure in the particle trap holder is irradiated with the particle beam so as to hold the microparticles. Thus, atmospheric microparticles can be efficiently condensed and captured in a relatively narrow space region. Then, the energy beam supply irradiates the particle trap with an energy beam to vaporize, sublimate, or react microparticles captured by the particle trap, thereby yielding a desorbed component. Therefore, energy can be concentrated to the captured atmospheric microparticles, and a desorbed component of a high concentration can be yielded in a short period of time. Then, the yielded desorbed component can be efficiently guided to the analyzer through the duct while being prevented from dispersing from the particle trap holder and analyzed. This allows the online quantitative analysis of the mass concentration of each chemical composition of atmospheric microparticles. Meanwhile, when the particle trap is irradiated with an energy beam, the atmospheric microparticles captured by the particle trap are desorbed in a short period of time, and the particle trap becomes ready to capture the subsequent microparticles. Therefore, online measurement can be performed with a high time resolution (several minutes to one hour) even with respect to an average atmospheric environment concentration level.

Further, the vacuum chamber includes a first partition for dividing a first space which includes the particle beam generator and a second space which includes the particle trap holder, the first partition includes a path of the particle beam, and the path of the particle beam and the particle beam entrance of the particle trap holder each have a skimmer configuration, whereby the first space and the second space can be decompressed so that the atmospheric pressure of the second space becomes lower than the atmospheric pressure of the first space. With this, the particle beam is efficiently introduced from the first space to the second space, and excess air can be removed in establishing a difference in pressure between the first space and the second space and maintaining the decompressed state of the first space. Further, the particle trap holder is allowed to receive a particle beam with an excess gas phase component removed therefrom.

Further, temperature control means is provided in the particle trap, whereby the temperature of the particle trap can be controlled to a temperature at which the evaporation of a highly volatile component of microparticles captured by the particle trap is reduced at a time of capturing the microparticles by the particle trap. With this, the highly volatile component can be captured and analyzed.

Further, a catalyst for converting the desorbed component into another substance is provided in a space of the duct, whereby the desorbed component can be converted into another substance in a series of processes in which the desorbed component is guided to the analyzer, and the converted substance can be analyzed. For example, a plurality of kinds of carbon compounds which are desorbed from an organic substance by heating are all oxidized to be converted into carbon dioxide, and the organic substance can be detected intensively and efficiently.

Further, a second partition for dividing a second space in which the particle trap holder is placed and a third space in which the analyzer is placed is provided in the vacuum chamber, the second and third spaces are decompressed so that the atmospheric pressure of the third space becomes lower than the atmospheric pressure of the second space, the duct is penetrated through the second partition, and the desorbed component in the particle trap holder is guided to the analyzer to generate a gentle air stream from the second space side to the third space side, whereby the desorbed component yielded by the irradiation with an energy beam can be efficiently guided to the analyzer.

Further, a flow path control mechanism is provided in the duct, and the flow path space of the duct is closed or narrowed down with the flow path control mechanism to decompress the third space to vacuum at the time of analysis of the desorbed component by the analyzer, whereby mass analysis in which an analysis unit must be a vacuum can be conducted. Further, when a highly volatile substance is analyzed, a particle trap portion can be set to be an atmospheric pressure, and the analysis unit can be set to be a vacuum.

Further, the duct is branched into a plurality of parts, whereby the desorbed component in the particle trap holder can be guided to a plurality of the analyzers.

In the apparatus for analyzing a microparticle composition of the present invention, it is preferred that the mesh-shaped structure be formed of a noble metal having a catalytic action. With this, the particle trap has a capturing action of capturing atmospheric microparticles efficiently and also has a catalytic action of converting the desorbed component into a form to be subjected to analysis.

In the apparatus for analyzing a microparticle composition of the present invention, it is preferred that the mesh-shaped structure include a first mesh-shaped structure having a predetermined porosity, which is placed on a front side of the particle trap which is a side which is to be irradiated with the particle beam, and a second mesh-shaped structure having a porosity smaller than that of the first mesh-shaped structure, which is placed on an opposite side (back side) of the particle trap which is a side opposite to the front side to be irradiated with the particle beam, the second mesh-shaped structure being connected to the first mesh-shaped structure. With this, microparticles having once entered a mesh-shaped structure can be captured by the first mesh-shaped structure, microparticles having passed through the first mesh-shaped structure can be captured by the second mesh-shaped structure, and microparticles having passed through the first mesh-shaped structure and having bounced off the second mesh-shaped structure can be captured by the first mesh-shaped structure. Thus, the microparticles can be prevented from flowing out and atmospheric microparticles can be captured efficiently.

In the apparatus for analyzing a microparticle composition of the present invention, it is preferred that the mesh-shaped structure include a front-side mesh-shaped structure having a predetermined porosity, which is placed on a front side of the particle trap which is a side which is to be irradiated with the particle beam, and a plate having no void, which is placed on an opposite side (back side) of the particle trap which is a side opposite to the front side to be irradiated with the particle beam, the plate being connected to the front-side mesh-shaped structure. With this, microparticles having once passed through the front-side mesh-shaped structure and having bounced off the plate can be captured by the front-side mesh-shaped structure. Thus, the microparticles can be prevented from flowing out and atmospheric microparticles can be captured efficiently.

Advantageous Effects of invention

According to the method of analyzing a microparticle composition of the present invention, a particle beam of microparticles in a gas sample is converged, having removed therefrom an excess gas phase component, and further a particle trap having a mesh-shaped structure is irradiated with the particle beam of microparticles in the gas sample to capture the microparticles. Therefore, atmospheric microparticles can be efficiently condensed and captured in a relatively narrow space region. Then, the particle trap is irradiated with an energy beam to vaporize, sublimate, or react the microparticles captured by the particle trap, thereby yielding a desorbed component. Therefore, energy can be concentrated to the captured atmospheric microparticles, and a desorbed component of a high concentration can be yielded in a short period of time and analyzed. This allows the online quantitative analysis of a mass concentration of each chemical composition of atmospheric microparticles. Meanwhile, when the particle trap is irradiated with an energy beam, the atmospheric microparticles captured by the particle trap are desorbed in a short period of time, and the particle trap becomes ready to capture the subsequent microparticles. Therefore, online measurement can be performed with a high time resolution (several minutes to one hour) even with respect to an average atmospheric environment concentration level.

According to the apparatus for analyzing a microparticle composition of the present invention, the particle beam generator forms a particle beam in which microparticles in gas are condensed in a beam shape, an excess gas phase component is removed, and the particle trap having a mesh-shaped structure in the particle trap holder is irradiated with the particle beam so as to hold the particle beam. Thus, atmospheric microparticles can be efficiently condensed and captured in a relatively narrow space region. Then, the energy beam supply irradiates the particle trap with an energy beam to vaporize, sublimate, or react microparticles captured by the particle trap, thereby yielding a desorbed component. Therefore, energy can be concentrated to the captured atmospheric microparticles, and a desorbed component of a high concentration can be yielded in a short period of time. Then, the yielded desorbed component can be efficiently guided to the analyzer through the duct while being prevented from dispersing from the particle trap holder and analyzed. This allow the online quantitative analysis of the mass concentration of each chemical composition of atmospheric microparticles. Meanwhile, when the particle trap is irradiated with an energy beam, the atmospheric microparticles captured by the particle trap are desorbed in a short period of time, and the particle trap becomes ready to capture the subsequent microparticles. Therefore, online measurement can be performed with a high time resolution (several minutes to one hour) even with respect to an average atmospheric environment concentration level.

DESCRIPTION OF EMBODIMENTS

Figure 1:
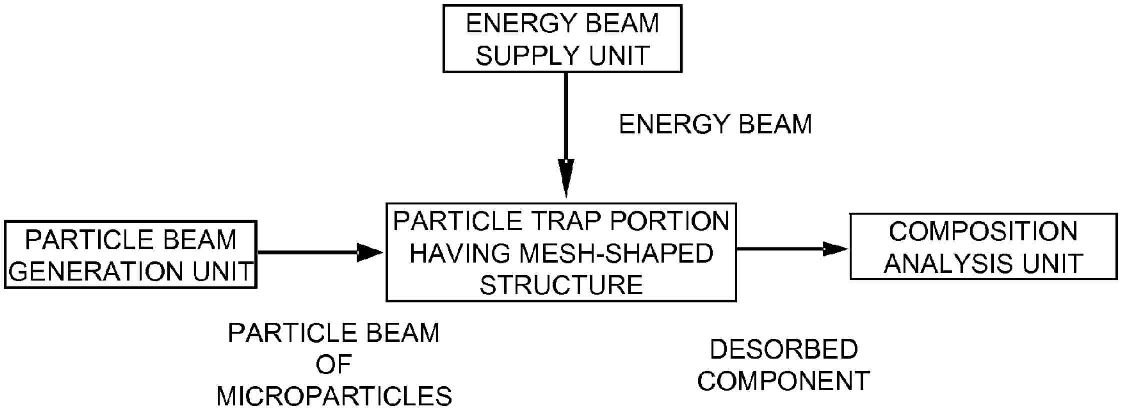
FIG. 1 A conceptual view of a method of analyzing a microparticle composition of the present invention.

FIG. 1 is a conceptual view illustrating a method of analyzing a microparticle composition of the present invention.

As illustrated in FIG. 1, in the method of analyzing a microparticle composition of the present invention, a particle beam of microparticles in a gas sample is converged in a particle beam generation unit, a narrow region of a particle trap portion having a mesh-shaped structure is irradiated with the particle beam while an excess gas phase component is being removed, and the microparticles are captured by the particle trap portion. Herein, the "narrow region" refers to a region that is narrow to such a degree as to provide energy to the captured microparticles efficiently upon irradiation with an energy beam described later. The narrow region preferably refers to a region of about 1 mm to 3 mm in terms of a diameter of a projected image having a circular shape in a cross-section of a particle beam formed by a surface to be irradiated of a particle trap into which microparticles are entered.

Further, a particle trap portion having a mesh-shaped structure is subjected to concentrated irradiation with an energy beam generated in an energy beam supply unit, and microparticles captured by the particle trap portion are vaporized, sublimated, or reacted by energy of the energy beam to yield a desorbed component. Herein, the "concentrated irradiation" refers to irradiating captured microparticles with an energy beam concentratedly to such a degree that the energy of the energy beam can be provided to the microparticles efficiently. The concentrated irradiation preferably refers to irradiation with an energy beam of about 0.1 mm to 5 mm in terms of a diameter of a projected image having a circular shape in a cross-section of an energy beam formed by a surface to be irradiated of a particle trap into which an energy beam is entered. In this case, a narrow region in which the microparticles are captured can also be irradiated with an energy beam so that the energy beam scans the region.

Further, the desorbed component yielded by vaporizing, sublimating, or reacting microparticles captured by the particle capture unit is guided to a composition analysis unit, and the desorbed component is analyzed in the composition analysis unit. Herein, the "desorbed component" refers to a component that is desorbed from a particle trap and becomes ready to move to the composition analysis unit. Specific examples of the desorbed component include $CO_2$, $H_2O$, $NO_2$, and $SO_2$ generated by oxidation of constituent components of microparticles.

In the method of analyzing a microparticle composition of the present invention, the above-mentioned energy beam may be selected or controlled depending upon energy absorption characteristics of constituent components of the microparticles. Specifically, when the constituent components of the microparticles are a sulfate, a nitrate, an organic substance, and the like, the microparticles are irradiated with an infrared laser, and when the constituent components of the microparticles are soot, a metal, and the like, the microparticles are irradiated with a visible or infrared laser. Thus, the present invention can handle microparticles with various chemical compositions.

In the present invention, a particle beam of microparticles in a gas sample refers to a particle beam of microparticles that are isolated and condensed into a beam shape from a gas sample (aerosol) in which microparticles are floating so that each microparticle has similar flight and movement characteristics in the gas sample, using aerodynamic characteristics of microparticles formed of a solid or a liquid. Such particle beam can be generated through use of a particle beam generator having a mechanism such as an orifice, a nozzle, or a combination thereof, such as an aerodynamic lens, for example, by placing one end of the particle beam generator outside a vacuum chamber, placing the other end in the vacuum chamber, and taking in external air by decompression of the vacuum chamber.

Figure 2:
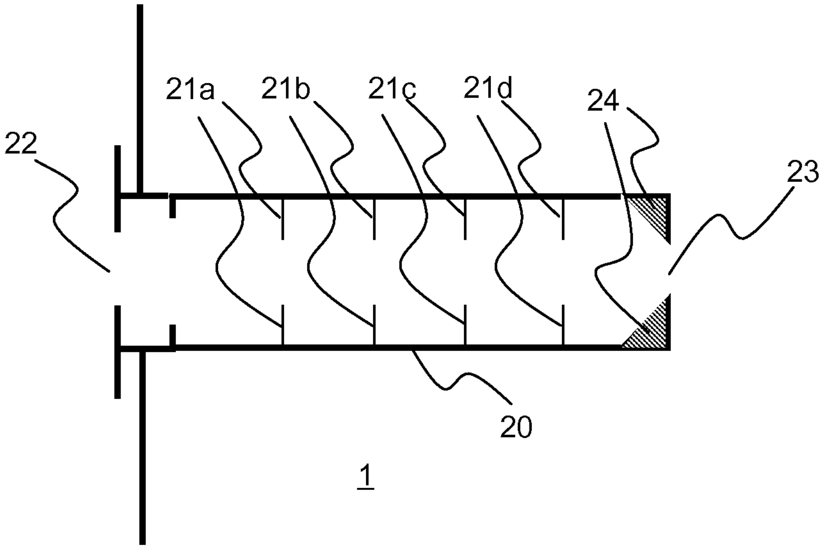
FIG. 2 A schematic view illustrating an example of an aerodynamic lens.

FIG. 2 is a schematic view illustrating a mechanism of an aerodynamic lens. An aerodynamic lens 1 has a structure in which several stages of orifices 21*a* to *d* are continuously provided in a tube-like housing 20, and a sample inlet 22 through which a gas sample flows in is provided on a side surface at one end, and a sample outlet 23 for discharging a generated particle beam of microparticles is provided on a side surface at the other end. In this figure, the sample inlet 22 is placed in the external air, and the sample outlet 23 is placed in a decompressed atmosphere. Due to the pressure difference, when a gas sample flows in from the external air side through the sample inlet 22 and passes through an aerodynamic lens, a gas that is a medium of the gas sample moves while dispersing, and hence, the gas is prevented from moving straight by the orifices 21. In contrast, microparticles formed of a solid or a liquid have high straight moving property compared with gas molecules. Therefore, the movement of the microparticles having passed through the orifice 21*a* in the initial stage is not prevented largely by the orifices 21*b* to 21*d* in the second and subsequent stages, and a particle beam of microparticles can be discharged to the decompressed atmosphere side through the sample outlet 23 while each microparticle is being converted into a beam shape. It should be noted that, in the aerodynamic lens 1, a nozzle 24 is provided at the sample outlet 23 so that the generated particle beam of microparticles is further focused and accelerated.

The size of microparticles capable of generating such beam-like particle beam depends upon the structure of an aerodynamic lens and pressure, and the microparticles having an aerodynamic diameter of about 3 μm or less are generally applicable. However, the application range of the method of analyzing a microparticle composition of the invention of the present application is not necessarily limited to the size of the microparticles. Further, a method of generating a particle beam of microparticles in a gas sample as well is not limited to a method using an aerodynamic lens.

Figure 3A:
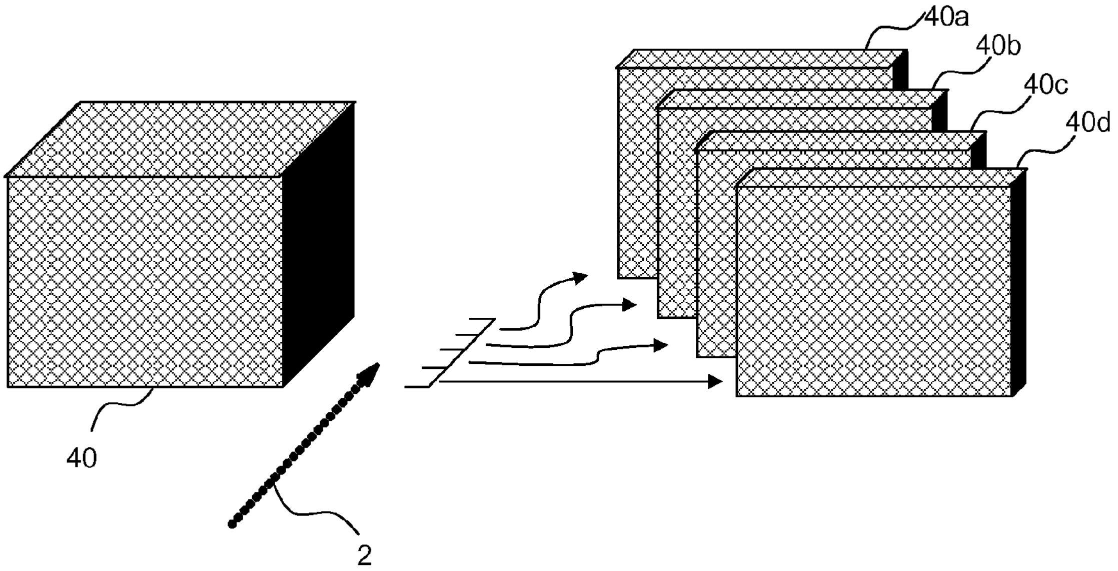
FIG. 3 A schematic view illustrating an example of a mesh-shaped structure of a particle trap (A); and an embodiment in which a plate having no void is placed so as to be connected to the mesh-shaped structure (B).

In the present invention, a particle trap having a mesh-shaped structure is a particle trap for capturing microparticles in the above-mentioned particle beam. FIG. 3(A) is a schematic view illustrating an example of a mesh-shaped structure of a particle trap usable in the present invention. As illustrated in FIG. 3(A), in terms of a structure, a mesh-shaped structure 40 can be considered to have a mesh-shaped structure as a whole, in which a plurality of mesh layers 40*a* to 40*d* are laminated. Then, the particle trap is irradiated with the above-mentioned particle beam of microparticles, individual microparticles pass through openings of the mesh layers to a certain depth at a specific probability (it is assumed that the particle trap is irradiated with a particle beam of microparticles 2 from the front side of the particle trap as illustrated in the figure, i.e., the side of the particle trap facing the front side of the page) and collide with the mesh layer positioned at the depth. Some of the particles are captured by the mesh layer, and others are bounced back while being decelerated. The bounced particles further collide with the mesh layer positioned on the front side of the particle trap. Some of the particles are captured by the mesh layer, and others are bounced back while being decelerated. After that, the bounced particles lose a speed before long while repeating the similar action and are captured by the above-mentioned particle trap.

Figure 3B:
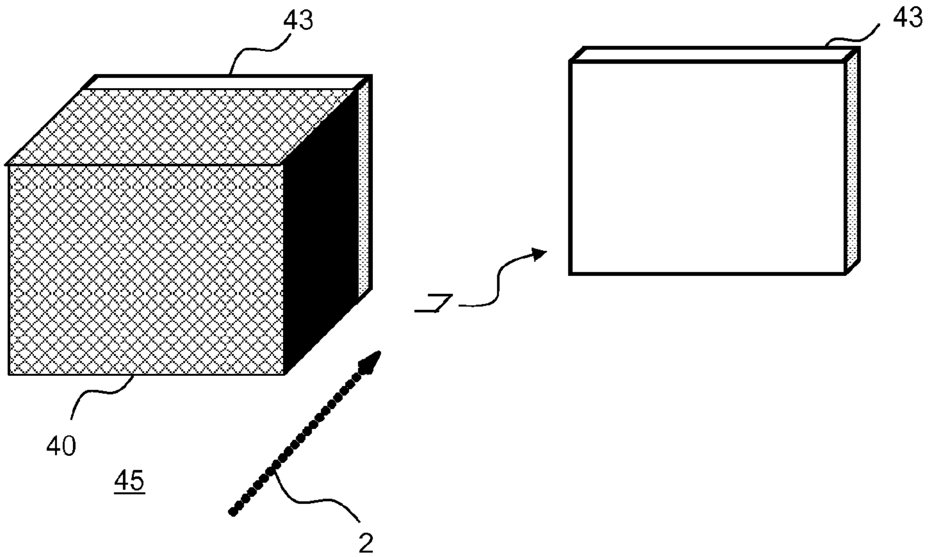

FIG. 3(B) illustrates a mesh-shaped structure 45 in which a plate having no void 43 is placed on the side of the mesh-shaped structure of FIG. 3(A) opposite to the side to be irradiated with a particle beam of microparticles, so as to be connected to the mesh-shaped structure. According to this embodiment, microparticles having once passed through the mesh-shaped structure and having been bounced back by the plate can be captured by the mesh-shaped structure.

It is preferred that a material for the mesh-shaped structure be a material whose structure does not change substantially even when the material is repeatedly irradiated with an energy beam for yielding a desorbed component by vaporizing, sublimating, or reacting the microparticles. With this, the mesh-shaped structure can withstand a plurality of uses. Thus, it is possible to perform the analysis of microparticles collected and accumulated over a predetermined period of time and the subsequent analysis of microparticles collected and accumulated over a predetermined period of time, and it is also possible to perform these analyses continuously. Examples of such material include platinum, gold, palladium, rhodium, iridium, and alloys thereof. It should be noted that these materials may be placed on the surfaces of the mesh-shaped structure, for example, by being formed as thin films on the surfaces of members used for a skeletal framework, a bony framework, and a framework for forming the mesh-shaped structure.

As such mesh-shaped structure, a structure formed of a non-woven fabric made of fibers of a metal, an alloy, or a compound thereof may be employed. For example, a commercially available platinum non-woven fabric "Platinum sheet" (average porosity: about 24%, thickness: about 0.1 mm, manufactured by Tanaka Kikinzoku Kogyo K.K.), or the like may be used.

Alternatively, as the mesh-shaped structure, a structure constructed of a microfabricated compact formed by laminating a plurality of mesh-shaped sheets formed by microfabrication may be employed. Such microfabricated compact may be obtained by, for example, microfabrication of silicon, a metal or the like.

Figure 5A:
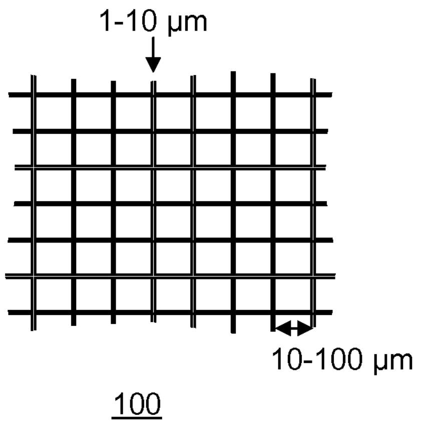
FIG. 5 An enlarged view of a mesh unit of a mesh structure substrate (A); a cross-sectional view of the mesh structure substrate taken along the line A-A' illustrated in FIG. 4(A) (B).
Figure 5B:
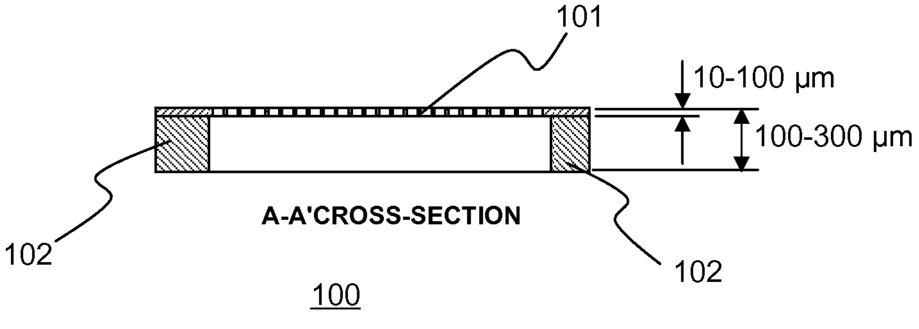
Figure 6:
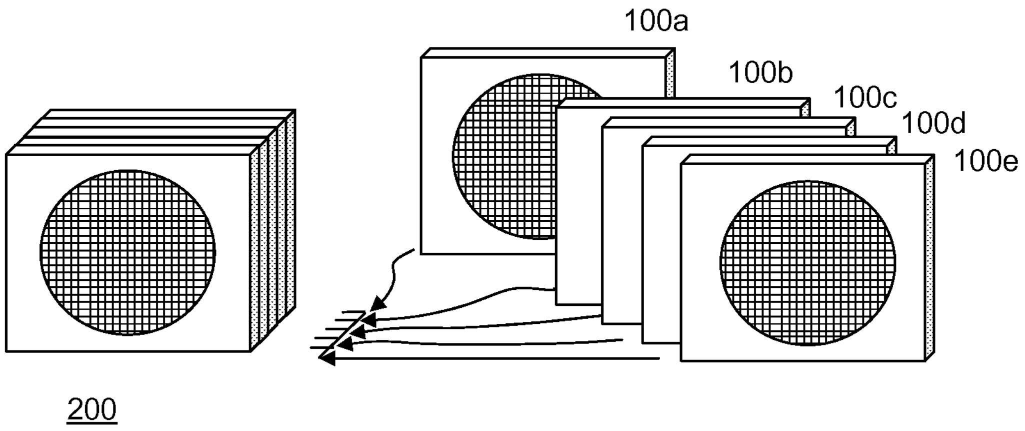
FIG. 6 A view illustrating that a plurality of mesh structure substrates are laminated to form a microfabricated compact having a mesh-shaped structure.

FIGS. 4 to 6 each illustrate an example of a mesh-shaped structure of a particle trap constructed of a microfabricated compact. This mesh-shaped structure is formed by attaching a plurality of mesh structure substrates, which are obtained by subjecting SOI substrates to photoetching, to each other so that the mesh structure substrates are laminated.

Figure 4A:
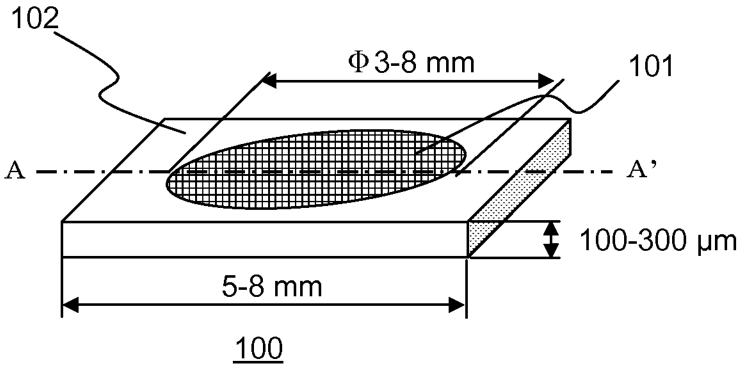
FIG. 4 A perspective view illustrating an example of a mesh structure substrate which forms the mesh-shaped structure of the particle trap, viewed from an upper side (A); and viewed from a lower side (B).
Figure 4B:
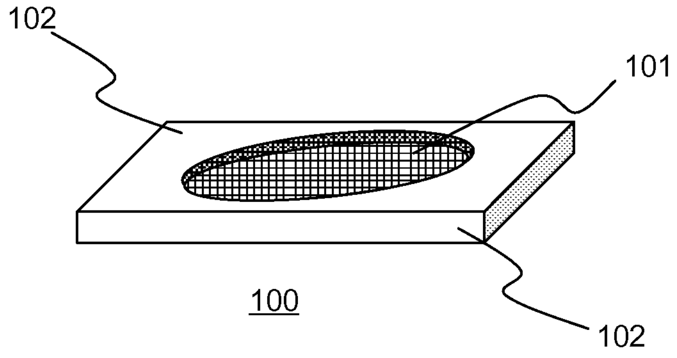

FIG. 4(A) is a perspective view of a mesh structure substrate 100, viewed from an upper side. Further, FIG. 4(B) is a perspective view of the mesh structure substrate 100, viewed from a lower side. The mesh structure substrate 100 includes a mesh 101 forming grid-like openings and a support frame 102 supporting the outer circumference of the mesh. The size of the mesh structure substrate 100 is typically about 5 to 8 mm square, the size of the region of the mesh 101 is about Φ3 to 8 mm, and the thickness of the support frame 102 is about 100 to 300 μm.

FIG. 5(A) is an enlarged view of a portion of the mesh. As illustrated in FIG. 5(A), the mesh has grid-like openings formed by microfabrication. The size of the grid is typically as follows: a frame width of about 1 to 10 μm; and a square opening of about 10 to 100 μm.

FIG. 5(B) is across-sectional view of the mesh structure substrate 100 taken along the line A-A' illustrated in FIG. 4(A). As illustrated together with FIG. 4(B), a space that is surrounded by the mesh 101 and the support frame 102 supporting the outer circumference of the mesh and that is hollowed out in a cylindrical shape is formed in a lower part of the mesh 101 by microfabrication. Herein, the thickness of the mesh 101 is typically about 10 to 100 μm, and the thickness of the support frame 102 is about 100 to 300 μm as described above.

FIG. 6 illustrates a microfabricated compact 200. The microfabricated compact 200 can be obtained by, for example, previously forming a thin film made of platinum, gold, palladium, rhodium, iridium, or an alloy thereof in a portion made of a silicon material of the mesh 101, and attaching a portion made of a silicon material of the support frame 102 via the thin film. In FIG. 6, the microfabricated compact 200 is formed by attaching a plurality of the mesh structure substrates 100 (five mesh structure substrates, i.e., mesh structure substrates 100*a* to 100*e*) to each other. As an attachment method, for example, the mesh structure substrates 100 may be adhered to each other via low-melting-point glass melted by heating at 300° C. to 500° C. Alternatively, the attachment may be performed by anodic bonding through use of glass substrates. Alternatively, a thin film made of platinum, gold, palladium, rhodium, iridium, an alloy thereof, or the like is formed in a portion made of a silicon material of the support frame 102 of the mesh structure substrate 100, and the mesh structure substrates 100 may be bonded to each other via the thin film layer. Alternatively, in the case where the material for the mesh structure substrate 100 is a metal, the mesh structure substrates 100 may be bonded to each other directly without using another material for adhesion. Alternatively, the mesh structure substrates 100 may be stacked simply in the case where the structure is allowed.

When one layer, or typically two to ten layers, preferably three to six layers of the mesh structure substrates 100 are attached to each other to be laminated to form the microfabricated compact 200, a mesh-shaped structure having a porosity of about 80 to 99% can be obtained. It should be noted that the mesh-shaped structure constructed of the microfabricated compact 200 has a structure in which a plurality of layers of mesh portions are laminated via spaces hollowed out into a cylindrical shape formed in a lower part of each mesh portion. Thus, the porosity of the mesh-shaped structure refers to a porosity per volume which the mesh portion occupies up to the depth when viewed from the direction in which microparticles are entered and does not include a cylindrical hollow and a support frame.

Although the square opening pattern of the mesh of the microfabricated compact 200 is typically a rectangular grid pattern, there is no particular limit to the shape and pitch of the pattern. A shape such as a circle, an ellipse, or a polygon may be employed and a combination of a plurality of shapes may be employed. A honeycomb structure or the like may be employed. Further, a shape, a pitch, or a phase thereof may be shifted or varied for each layer to be laminated.

In the present invention, it is preferred that the mesh-shaped structure include a first mesh-shaped structure having a predetermined porosity, which is placed on the front side of the particle trap which is a side which is to be irradiated with the particle beam, and a second mesh-shaped structure having a porosity smaller than that of the first mesh-shaped structure, which is placed on the opposite side (back side) of the particle trap which is a side opposite to the front side to be irradiated with the particle beam.

Figure 7A:
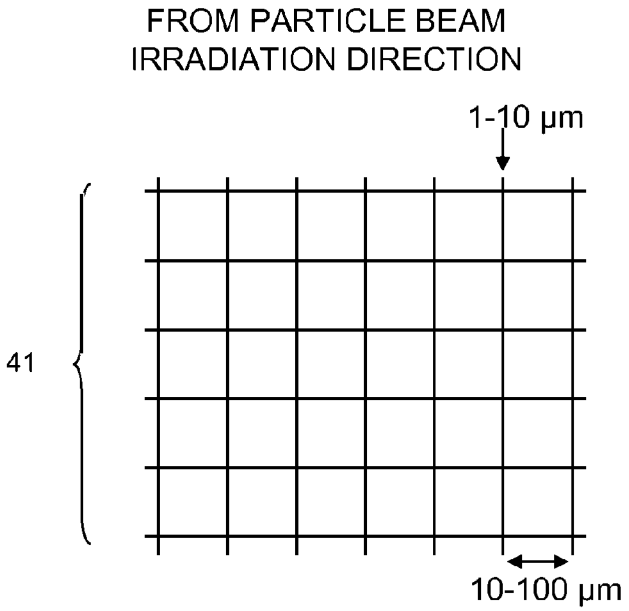
FIG. 7 A schematic view illustrating another example of the mesh-shaped structure of the particle trap, from a particle beam irradiation direction (A); and from a cross-sectional direction of the particle trap (B).
Figure 7B:
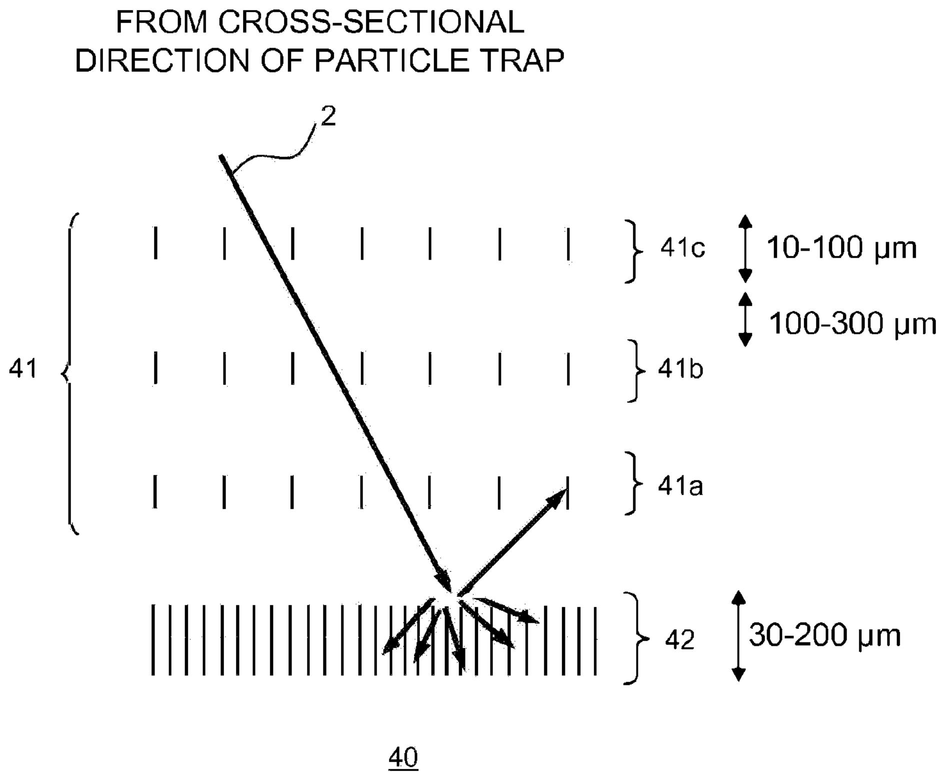

FIG. 7 illustrates an example of another mesh-shaped structure thus configured. FIG. 7(A) is a schematic view from a particle beam irradiation direction, and FIG. 7(B) is a schematic view from a cross-sectional direction of a particle trap.

In the mesh-shaped structure 40, a first mesh-shaped structure 41 having a relatively large porosity is placed on the front side of the particle trap is which is a side which is to be irradiated with a particle beam. Further, a second mesh-shaped structure 42 having a porosity smaller than that of the first mesh-shaped structure is placed on the side (back side) of the particle trap which is a side opposite to the front side to be irradiated with a particle beam. As the first mesh-shaped structure 41, there may be used one which is obtained by the above-mentioned microfabrication forming and is constructed of a microfabricated compact having a size of about 3 to 8 mm square, a grid size of: a frame width of about 1 to 10 μm; and a square opening of 10 to 100 μm, a grid thickness of about 10 to 100 μm, a spacer thickness of about 100 to 300 μm, and the number of layers of about 1 to 10. In such microfabricated compact, the porosity of the mesh-shaped structure is about 80 to 99% as described above. Further, as the second mesh-shaped structure 42, the above-mentioned platinum non-woven fabric “Platinum sheet” (average porosity: about 24%, thickness: about 0.1 mm, manufactured by Tanaka Kikinzoku Kogyo K.K.) or the like may be used.

According to this embodiment, the porosity of the first mesh-shaped structure 41 is set to be relatively large. Hence, the the probability that the microparticles in the particle beam bounce off the surface of the particle trap is small, and the microparticles easily reach the inside of the first mesh-shaped structure 41 and the second mesh-shaped structure 42. Then, the microparticles are captured by the first or second mesh-shaped structure. Alternatively, even when bouncing off the second mesh-shaped structure 42, the microparticles collide with any grid layer (41*a*, 41*b*, or 41*c* in FIG. 7(B)) forming the first mesh-shaped structure 41, and thus are reduced in speed and captured. Therefore, the microparticles can be captured reliably in the void of the mesh-shaped structure 40.

In another embodiment of the present invention, it is preferred that the mesh-shaped structure have a mesh-shaped structure having a predetermined porosity, which is placed on a front side of the particle trap which is a side which is to be irradiated with the particle beam, and a plate having no void, which is placed on a side (back side) of the particle trap which is a side opposite to the front side to be irradiated with the particle beam to be connected to the mesh-shaped structure.

Figure 8A:
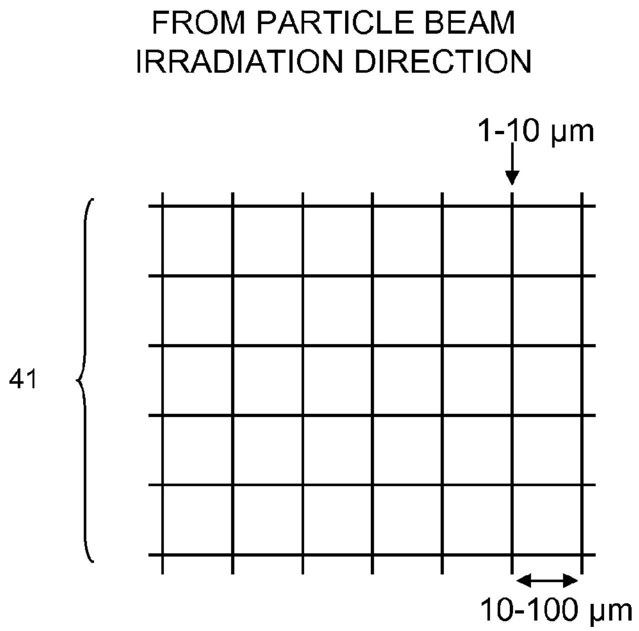
FIG. 8 A schematic view illustrating still another example of the mesh-shaped structure of the particle trap, from a particle beam irradiation direction (A); and from a cross-sectional direction of the particle trap (B).
Figure 8B:
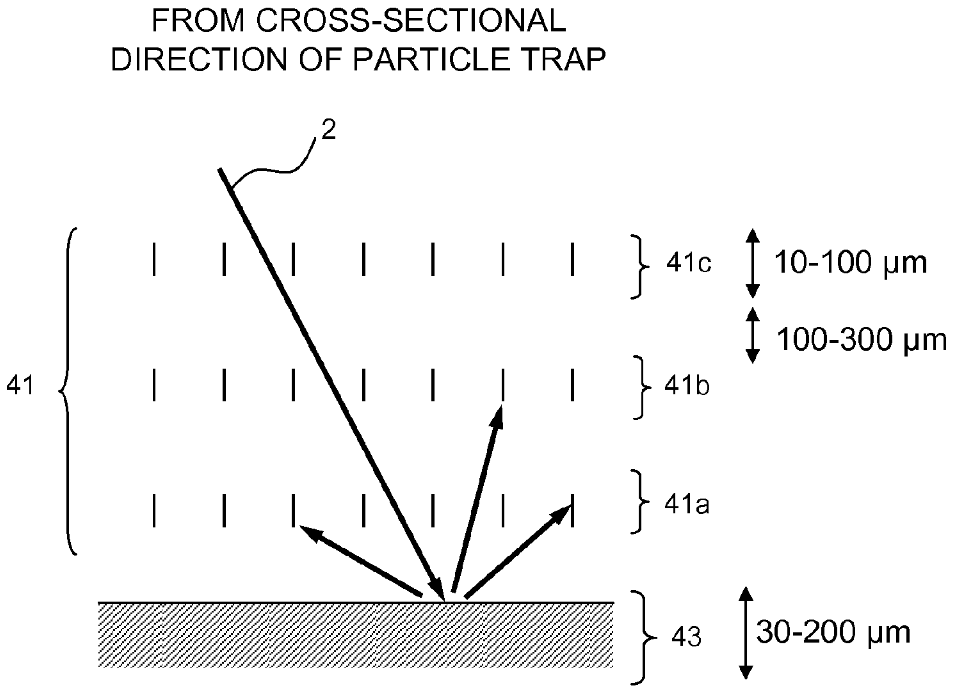

FIG. 8 illustrates an example of the mesh-shaped structure thus configured. FIG. 8(A) is a schematic view from a particle beam irradiation direction, and FIG. 8(B) is a schematic view from a cross-sectional direction of a particle trap.

In the mesh-shaped structure 45, the first mesh-shaped structure 41 having a relatively large porosity described in FIG. 7 is placed on the front surface side to be irradiated with the particle beam. Further, on the side opposite to the side to be irradiated with the particle beam, the plate having no void 43 is placed in place of the second mesh-shaped structure 42 described in FIG. 7. The plate 43 may be made of a material that reflects microparticles, and specifically, platinum, gold, palladium, rhodium, iridium, or an alloy thereof can be used. Further, it is preferred that the surface of the material have irregularities which cause the diffuse reflection of microparticles.

According to this embodiment, the porosity of the first mesh-shaped structure 41 is set to be relatively large. Hence, the probability that the microparticles in the particle beam bounce off the surface of the particle trap is small, and the microparticles easily reach the inside of the first mesh-shaped structure 41 and the plate 43. Then, the microparticles are captured by the first mesh-shaped structure. Alternatively, when bouncing off the plate 43, the microparticles collide with any grid layer (41*a*, 41*b*, or 41*c* in FIG. 8(B)) forming the first mesh-shaped structure 41, and thus are reduced in speed and captured. Therefore, the microparticles can be captured reliably in the void formed of the first mesh-shaped structure 41 and the plate 43.

Another embodiment of the particle trap may include a mesh-shaped structure for capturing microparticles from a particle beam of microparticles, including a first mesh-shaped structure, which is placed on a front side of the particle trap which is a side which is to be irradiated with a particle beam, and a second mesh-shaped structure or a plate having no void, which is placed on the back side of the particle trap which is the side opposite to the front side to be irradiated with a particle beam, in which the first mesh-shaped structure is formed of a mesh-shaped structure having a predetermined porosity and the second mesh-shaped structure is formed of a mesh-shaped structure having a porosity smaller than that of the first mesh-shaped structure.

In this case, the first mesh-shaped structure and the second mesh-shaped structure may be constructed of an integrated mesh-shaped structure that is formed in such a manner that the porosity becomes smaller from a side to be irradiated with a particle beam to the back side gradually, step-by-step, or in a layered shape with a hollow sandwiched therein. Further, the first mesh-shaped structure and the second mesh-shaped structure may each be constructed of a mesh-shaped structure that is formed in such a manner that the porosity changes gradually, step-by-step, or in a layered shape with a hollow sandwiched therein.

Further, it is preferred that the first mesh-shaped structure have a porosity of about 80 to 99%.

Further, it is preferred that the first mesh-shaped structure include a laminate of a plurality of mesh structure substrates formed of a mesh having a grid-like opening and a support frame for supporting the outer circumference of the mesh. The number of layers in the mesh structure substrates is typically 2 to 10, preferably 3 to 6. It should be noted that a hollow in a lamination interval portion and a volume of the support frame are not included in the porosity.

In this case, regarding each single mesh substrate, it is preferred that an areal porosity obtained by projecting a mesh onto a surface orthogonal to a predetermined first direction (for example, a direction perpendicular to a substrate when the substrate is flat) when viewed from a side to be irradiated with a particle beam be about 80 to 99%. Further, it is preferred that an areal porosity obtained by projecting a mesh onto a surface orthogonal to a second direction that is away from the first direction by a predetermined angle (for example, about 45°) be smaller than the above-mentioned areal porosity. In order to realize this, it is preferred to set a grid frame of the mesh having a grid-like opening, for example, so that a line width viewed from a plane direction of the grid frame is 1 to 10 μm, a height viewed from a side surface direction of the grid frame is 10 to 100 μm, and a pore diameter width by the grid frame is 10 to 100 μm. Further, it is preferred that the interval of the meshes laminated in the first mesh-shaped structure be set to 100 to 300 μm.

With the above-mentioned configuration, the first mesh-shaped structure is set to have a relatively large areal porosity viewed from a side to be irradiated with a particle beam. Hence, the probability that microparticles bounce off the surface of the particle trap is small, and the microparticles easily reach the inside of the mesh-shaped structure. Then, the microparticles having once entered the inside bounce at a certain angle. Therefore, the microparticles are captured in a portion on a side surface of the grid frame or bounce further to collide another portion to have the speed weakened and captured. Thus, the microparticles can be prevented from flowing out, and atmospheric microparticles can be captured efficiently.

Further, the porosity and the lamination interval of the mesh-shaped structure which includes a laminate of a plurality of the mesh structure substrates are set to be relatively large. Therefore, an energy beam to be applied so as to yield a desorbed component of microparticles easily reaches the inside, and energy of the energy beam is allowed to efficiently spread to the entire mesh-shaped structure capturing microparticles. For example, in the case where the energy beam is laser light, the energy beam is allowed to spread efficiently by using reflection, diffraction, or the like in a frame or by scanning an irradiation direction.

In the present invention, the temperature of the particle trap upon irradiation with the particle beam of microparticles can also be controlled to a temperature at which the evaporation of a highly volatile component of the microparticles captured by the particle trap is reduced. The temperature can be controlled by forming a particle trap supporting portion (described later) which is brought into contact with the particle trap and supports the particle trap through use of a thermally conductive material such as copper and embedding a thermocouple thermometer and a Peltier cooling element in the particle trap supporting portion. Thus, the highly volatile component can be captured and analyzed.

For example, in the case where a highly volatile nitrate or partial organic substance (hydrocarbon, etc.) is to be measured, the evaporation can be avoided substantially by lowering the temperature of a particle trap to a range of −20 to 0° C.

In the present invention, there is no particular limit to an energy beam as long as it vaporizes, sublimates, or reacts microparticles captured by the particle trap to yield a desorbed component suitable for analyzing the composition of the microparticles. It is preferred that the energy beam be supplied by, for example, an infrared laser supply, a visible laser supply, an ultraviolet laser supply, an X-ray supply, and an ion beam supply. With this, energy can be concentrated to a narrower region by laser light, an X-ray, or an ion beam to yield a desorbed component of the microparticles efficiently.

In the present invention, the kind, wavelength, intensity, and the like of the energy beam can be selected depending upon energy absorption characteristics of a component previously set as a detection target. This allows the simultaneous quantitative analysis of a plurality of components as well.

The particle trap from which the desorbed component has been yielded desorbs microparticles and becomes ready to collect and accumulate to capture the subsequent microparticles. Thus, as described above, after microparticles collected and accumulated over a predetermined period of time are analyzed, microparticles collected and accumulated over the subsequent predetermined period of time can be further analyzed. Further, these analyses can also be conducted continuously. At this time, an operation mode of further irradiating a particle trap with a first energy beam for yielding a desorbed component and heating a component remaining in the particle trap at high temperature to clean the particle trap more completely may be provided separately from the operation mode of performing irradiation with a particle beam of microparticles and analysis. Further, for cleaning the particle trap, the particle trap may be irradiated with a second energy beam for heating the component remaining in the particle trap at high temperature to clean the particle trap more completely, separately from the energy beam used for yielding a desorbed component of microparticles.

In the present invention, there is no particular limit to the means for analyzing the desorbed component, and analysis means that can be used by those skilled in the art can be selected and used appropriately. In particular, for online measurement, means having a mechanism that detects a signal corresponding to a molecular kind of the desorbed component in a moment or with a high time resolution is preferred. For example, mass analysis, spectrometry, or the like can be exemplified preferably. Further, a combination of these analyses may be conducted.

In the present invention, the desorbed component can be converted into another substance through use of a catalyst, and the converted substance can be analyzed. Examples of the material for the catalyst include platinum, gold, palladium, rhodium, iridium, and a compound or an alloy thereof.

The desorbed component can be converted into another substance through use of a catalyst by placing a catalyst in a flow path of a duct (described later) connected to a particle trap holder and bringing the desorbed component into contact with the catalyst while the desorbed component is being guided to an analysis unit.

Further, the mesh-shaped structure may be formed of a noble metal having a catalytic action. According to this configuration, the particle trap has a capturing action of capturing atmospheric microparticles efficiently and also has a catalytic action of converting the desorbed component into a form to be subjected to analysis. Examples of such noble metal include, in addition to platinum of the platinum non-woven fabric, gold, palladium, rhodium, iridium, and an alloy thereof. It should be noted that these materials may be placed on the surfaces of the mesh-shaped structure, for example, by being formed as thin films on the surfaces of members used for a skeletal framework, a bony framework, a framework, and the like for forming the mesh-shaped structure.

Next, one embodiment of an apparatus for analyzing a microparticle composition of the present invention is described with reference to FIG. 9.

In the apparatus for analyzing a microparticle composition 50, vacuum chambers 11*a*, 11*b*, and 11*c* are partitioned by a first partition 12 and a second partition 13 and form a vacuum chamber 11 divided into three chambers as a whole. The vacuum chambers 11*a*, 11*b*, and 11*c* are respectively decompressed with evacuation devices 14*a*, 14*b*, and 14*c*. In addition, the first partition 12 for dividing the vacuum chambers 11*a* and 11*b* is provided with a communication port which forms a skimmer 3 described later, and the second partition 13 for dividing the vacuum chambers 11*b* and 11*c* is provided with a communication port in a portion of a duct 8 described later. The vacuum chamber 11 is capable of forming a state in which the inside of the chamber is decompressed with respect to an external air atmosphere, and a predetermined air stream can be generated by adjusting the degree of decompression of each of the vacuum chambers 11*a* to 11*c* by each of the evacuation devices 14*a* to 14*c*. The vacuum chambers 11*a*, 11*b*, and 11*c* provide a first space, a second space, and a third space having different atmospheric pressures, respectively.

Further, the aerodynamic lens 1 that is a particle beam generator that generates a particle beam of microparticles in gas, described in FIG. 2, is provided passing through a side wall which is brought into contact with the external air atmosphere of the vacuum chamber 11*a* so as not to impair decompression. A sample inlet 22 at one end of the aerodynamic lens 1 is placed outside of the chamber of the vacuum chamber 11, and a sample outlet 23 at the other end is placed in the chamber of the vacuum chamber 11*a*.

The sample outlet 23 placed in the chamber of the vacuum chamber 11*a* is directed to the communication port formed at the first partition 12 between the vacuum chambers 11*a* and 11*b* so that the generated particle beam of microparticles 2 reach the inside of the chamber of the vacuum chamber 11*b* through the communication port. Further, the evacuation devices 14*a*, 14*b*, and the first partition 12 make an adjustment so that the atmospheric pressure in the second space provided by the vacuum chamber 11*b* becomes lower than the atmospheric pressure in the first space provided by the vacuum chamber 11*a*. Thus, an air stream from the vacuum chamber 11*a* to the vacuum chamber 11*b* is generated, which assists the flight of the particle beam of microparticles 2 from the vacuum chamber 11*a* side to the vacuum chamber 11*b* side.

Further, the communication port formed at the partition between the vacuum chambers 11*a* and 11*b* is the skimmer 3 formed so as to be tapered to narrow toward the direction in which the particle beam of microparticles 2 is entered, whereby the particle beam 2 is introduced efficiently from the vacuum chamber 11*a* to the vacuum chamber 11*b* while an excess gas phase component is removed. Further, the opening of the skimmer 3 is tapered to narrow, which assists a difference in pressure between the atmospheric pressure in the first space provided by the vacuum chamber 11*a* and the atmospheric pressure in the second space provided by the vacuum chamber 11*b* to be kept.

Next, a particle trap and a particle trap holder are described with reference to FIG. 10.

Figure 10A:
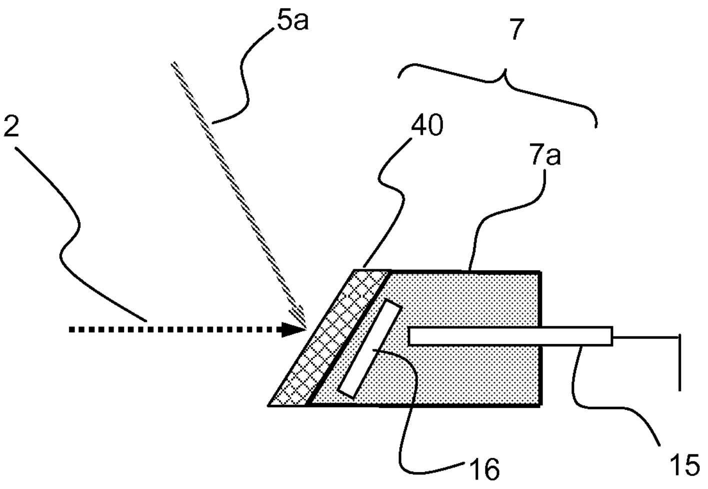
FIG. 10 An enlarged view of a particle trap (A); and an enlarged view of a particle trap holder (B).

FIG. 10(A) is an enlarged view of a particle trap. In this example, a particle trap 7 is constructed of a mesh-shaped structure 40 and a particle trap supporting portion 7*a* supporting the mesh-shaped structure 40. A support surface inclined diagonally is formed on one side surface of the particle trap supporting portion 7*a*, and the mesh-shaped structure 40 is placed on the support surface. Thus, both an angle at which the particle beam of microparticles 2 is entered into the particle trap 7 and an angle at which a laser 5*a* from the energy beam supply 5 is entered into the particle trap 7 are adjusted, whereby both the capture efficiency of microparticles by the particle trap 7 and the generation efficiency of the desorbed component of microparticles by the energy beam can be optimized.

Further, this embodiment includes a temperature control mechanism for controlling the temperature of the mesh-shaped structure 40. More specifically, the particle trap supporting portion 7*a* is formed of a metal having a high thermal conductivity such as copper, and a thermocouple temperature sensor 15 and a Peltier cooling element 16 are embedded therein. Then, when microparticles are captured by the particle trap, the temperature of the particle trap can be lowered to a temperature at which the evaporation of a highly volatile component of the microparticles captured by the particle trap is reduced. Further, when an energy beam is applied, cooling is stopped so as to raise a temperature. This is convenient for capturing and analyzing a highly volatile component.

Figure 10B:
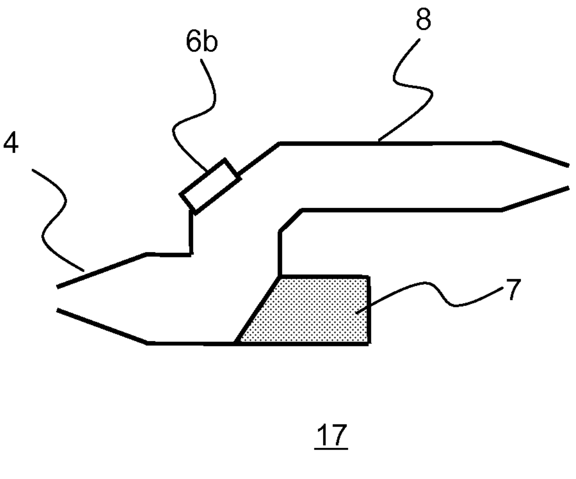

FIG. 10(B) is an enlarged view of a particle trap holder. A particle trap holder 17 holds the particle trap 7 integrally. In addition, in this embodiment, the particle trap holder 17 is provided with a skimmer portion 4 formed so as to be tapered to narrow toward a direction in which the particle beam of microparticles 2 is entered. Further, a duct 8 for supplying a desorbed component of microparticles to an analyzer 10 is formed integrally. Further, an optical window 6*b* is provided on one side wall of the particle trap holder 17.

Figure 9:
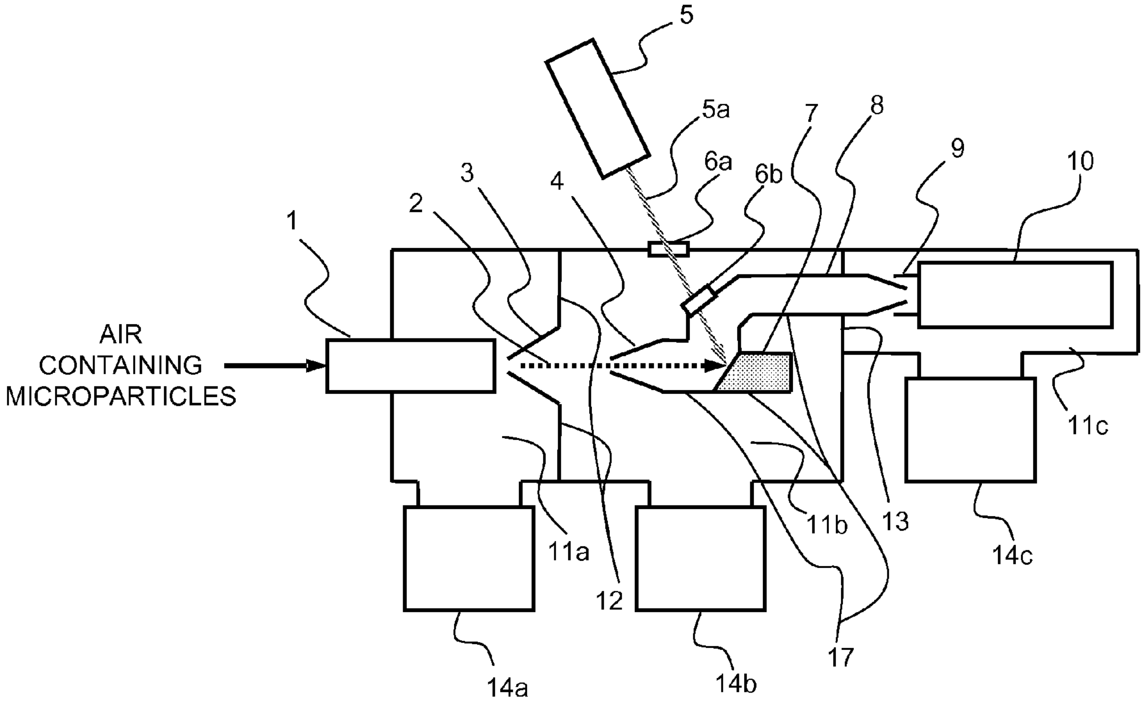
FIG. 9 A view illustrating one embodiment of an apparatus for analyzing a microparticle composition of the present invention.

In the embodiment illustrated in FIG. 9, in the chamber of the vacuum chamber 11*b*, the particle trap 7 described in FIG. 10 is held by the particle trap holder 17 holding the particle trap and placed at a position where the particle beam of microparticles 2 emitted from the sample outlet 23 of the aerodynamic lens 1 is applied, and microparticles constituting the particle beam of microparticles 2 are captured by the particle trap 7. At this time, the particle beam 2 is introduced efficiently toward the particle trap in the particle trap holder while an excess gas phase component is removed by the skimmer portion 4 of the particle trap holder 17 in the same way as in the above-mentioned skimmer 3.

Further, the laser supply 5 as an energy beam supply is placed outside of the vacuum chamber 11. The laser 5*a* is applied to the particle trap 7 through an optical window 6*a* formed on a side wall which is brought into contact with the external air atmosphere of the vacuum chamber 11*b* and an optical window 6*b* formed on one side wall of the particle trap holder 17, and the microparticles captured by the particle trap are vaporized, sublimated, or reacted by the irradiation with the laser 5*a*, whereby a desorbed component can be generated.

As described above, in the chamber of each of the vacuum chambers 11*a* to 11*c*, a predetermined air stream can be generated by the control of each of the evacuation devices 14*a* to 14*c*. In the embodiment illustrated in FIG. 9, the evacuation devices 14*b*, 14*c* and the second partition 13 make an adjustment so that the atmospheric pressure of the third space provided by the vacuum chamber 11*c* becomes lower than that of the second space provided by the vacuum chamber 11*b*. Thus, an air stream from the vacuum chamber 11*b* to the vacuum chamber 11*c* is generated, whereby a desorbed component generated by the irradiation with the laser 5*a* is guided to a composition analysis unit.

At this time, the particle trap holder 17 also functions so as to prevent the desorbed component generated by the irradiation with the laser 5*a* from dispersing into the chamber of the vacuum chamber 11*b*. More specifically, as described above, an end of the particle trap holder 17 on the vacuum chamber 11*c* side extends to integrally form the duct 8 for guiding the desorbed component to the vacuum chamber 11*c*. Then, the duct 8 passes through the second partition 13 that partitions the vacuum chambers 11*b* and 11*c*, and the end is placed in the chamber of the vacuum chamber 11*c*. Further, the end is tapered to narrow, thereby assisting a difference in pressure between the atmospheric pressure of the second space provided by the vacuum chamber 11*b* and the atmospheric pressure of the third space provided by the vacuum chamber 11*c* to be kept. Thus, the desorbed component generated by the irradiation with the energy beam can be guided to the composition analysis unit efficiently without dissipating into the chamber of the vacuum chamber 11*b*.

In the embodiment illustrated in FIG. 9, a mass spectrometer 10 is placed in the chamber of the vacuum chamber 11*c*. A sample introducing unit of the mass spectrometer 10 is provided with an ionization region 9, and further, an outlet of the duct 8 is placed at a position close to the ionization region 9. Thus, the desorbed component generated by the irradiation with the energy beam moves from the outlet through the duct 8 to the ionization region 9, and then is ionized and subjected to analysis in the mass spectrometer 10.

Figure 11:
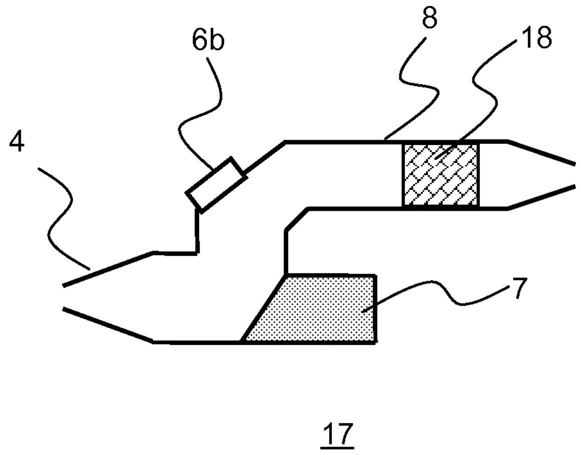
FIG. 11 A view illustrating another example of a particle trap holder used in the present invention and a duct connected thereto.

FIGS. 11 and 12 each illustrate another example of the particle trap holder 17 used in the present invention and the duct 8 connected thereto.

In FIG. 11, a catalyst 18 for converting a desorbed component of microparticles into another substance is placed inside of a space of the duct 8. In this example, the catalyst 18 is a honeycomb structure having a pore through which a desorbed component of microparticles can pass, and the desorbed component of microparticles is brought into contact with the catalyst while being guided to an analysis unit. As the catalyst, for example, a platinum catalyst having an oxidation catalysis action can be used. In this case, it is preferred that the catalyst be heated to about 100 to 400° C. to enhance the oxidation catalysis action of the catalyst. When an oxidation catalyst is used, for example, a plurality of kinds of carbon compounds which are desorbed from an organic substance by heating are all oxidized and carbon thereof can be consolidated into carbon dioxide. Therefore, the concentration of an organic substance in a gas sample can be quantified efficiently.

Figure 12A:
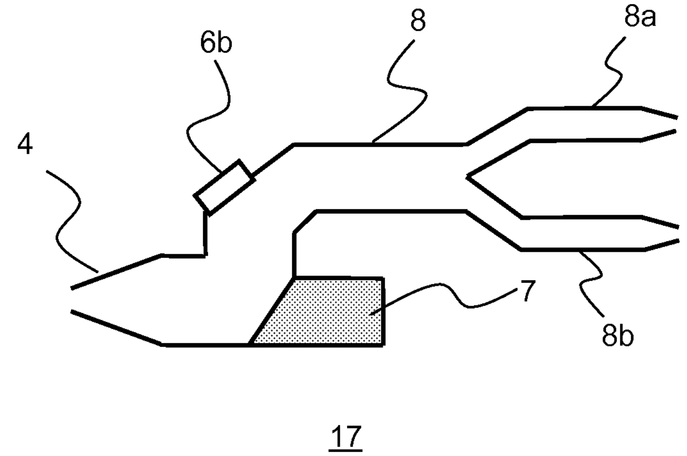
FIG. 12 A view illustrating still another example of a particle trap holder used in the present invention and a duct connected thereto.
Figure 12B:
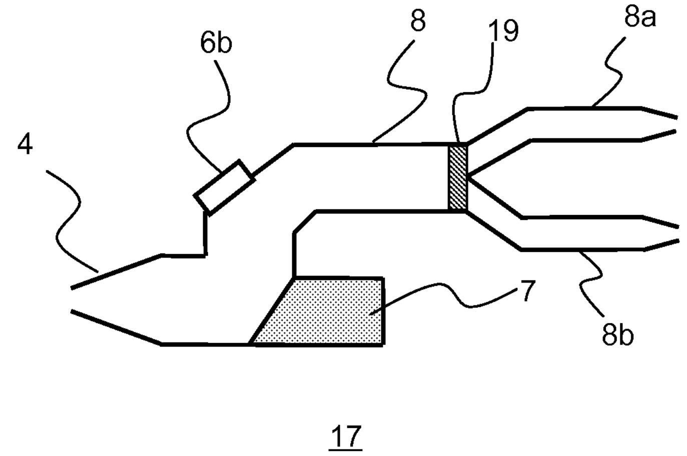
Figure 12C:
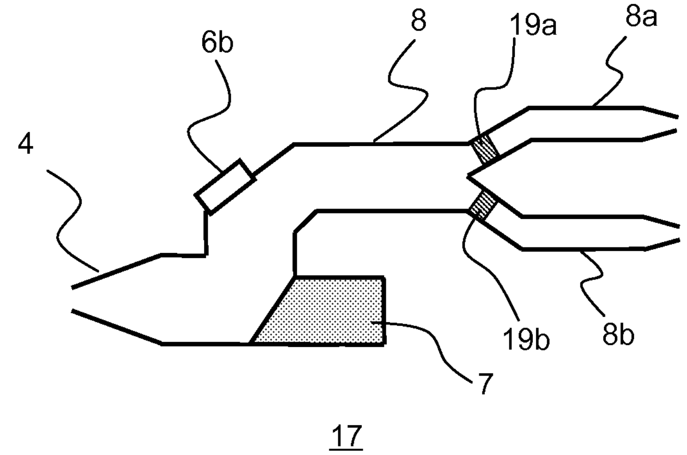

In FIG. 12(A), the duct 8 is provided with a flow path control mechanism. More specifically, the duct 8 is branched into two ducts 8*a* and 8*b*, whereby a desorbed component of microparticles can be guided to a plurality of the analyzers. Further, in FIG. 12(B), a branched portion is further provided with a valve 19 which can close or narrow down the flow path space of the duct 8. In this case, if required, the valve 19 may be configured so as to guide a desorbed component to analyzers respectively connected to the ducts 8*a*, 8*b* at different ratios. Further, as illustrated in FIG. 12(C), the branched ducts 8*a*, 8*b* can also be provided with two valves 19*a*, 19*b*, respectively. The catalyst 18 can also be placed in any one or both of the branched ducts 8*a*, 8*b*.

Further, for example, in the case of using a mass spectrometer as an analyzer, it is requested that the analysis be conducted in a vacuum atmosphere. In the embodiment illustrated in FIG. 9, the tip end of the duct 8 is tapered, and an opening thereof is a pinhole having a diameter of about 3 mm, which assists the third space provided by the vacuum chamber 11*c* to be kept in vacuum. In another embodiment, when a desorbed component is analyzed by the analyzer, the flow path space of the duct 8 can be closed or narrowed down by the valve 19 or the like to decompress the third space to vacuum.

EXAMPLES

Hereinafter, the present invention is described in more detail by way of examples. However, these examples do not limit the scope of the present invention.

Test Example 1

Measurement of Sulfate Aerosol

An apparatus for analyzing a microparticle composition having a configuration of an apparatus for analyzing a microparticle composition 50 illustrated in FIG. 9 was produced, and the mass concentration of ammonium sulfate particles in a gas was quantified. An aerosol containing monodisperse ammonium sulfate particles was generated by spraying and drying an ammonium sulfate aqueous solution to generate polydisperse particles, and then the polydisperse particles were allowed to pass through a classification device of a differential mobility analyzer (DMA).

The apparatus for analyzing a microparticle composition was adjusted so that the pressures in the chambers of the vacuum chambers 11*a*, 11*b*, and 11*c* were set to be $10^{-3}$ to $10^{-2}$ [Torr], $10^{-5}$ to $10^{-4}$ [Torr], and $10^{-7}$ to $10^{-6}$ [Torr], respectively, and the flow rate of a gas to be introduced into the aerodynamic lens 1 was 80 to 90 [cc/min]. After air as a carrier gas was preliminary introduced, a three-way valve was switched to start introducing the aerosol containing the ammonium sulfate particles, and the three-way valve was switched again after 10 minutes to switch to air as a carrier gas, thereby stopping the introduction of the aerosol. After that, the laser supply 5 was operated to irradiate the particle trap 7 with a laser for 2 minutes, and a desorbed component was measured by the mass spectrometer 10. The aerosol containing ammonium sulfate particles was introduced continuously from the start. Mass peaks were measured at m/z 48 (signal of SO) and m/z 64 (signal of $SO_2$) as the main mass peaks of a sulfate.

Figure 13:
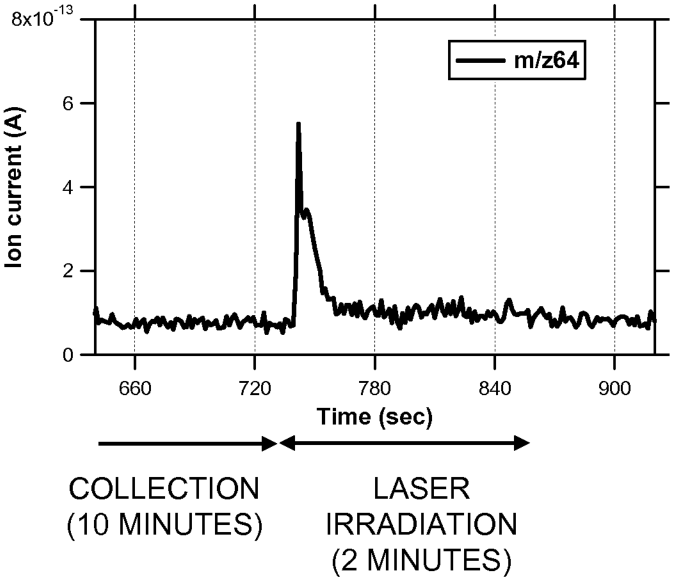
FIG. 13 A chart showing a change with time of an ion signal at a mass peak m/z 64.

FIG. 13 shows the result of measurement of the mass peak m/z 64. As a result, immediately (about 5 seconds) after the irradiation with a laser, a signal reached a peak, and then, the signal substantially converged by 30 seconds after the laser irradiation. Thus, it was clarified that a desorbed component was able to be generated from the particle trap 7 instantly by the laser irradiation, and the analysis was able to be completed with a high time resolution. It should be noted that, although the result of the mass peak m/z 48 was not shown, the result was almost proportional to the result of the mass peak m/z 64, and thus, the similar result was obtained.

Test Example 2

Linearity and Quantitativity of Measurement

Figure 14:
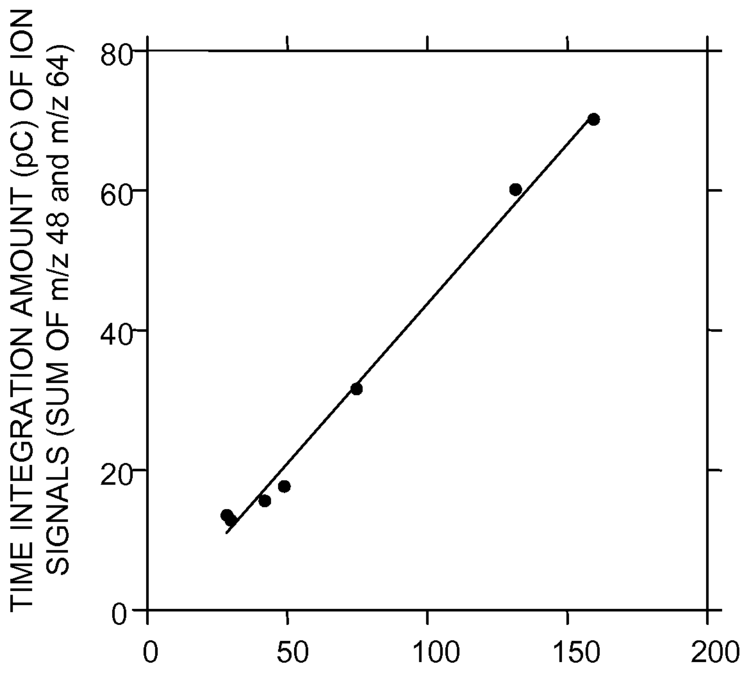
FIG. 14 A graph showing a positive correlation between an accumulated mass of microparticles and a time integration amount of ion signals for ammonium sulfate particles.

A test similar to Test Example 1 was conducted by changing the mass concentration of ammonium sulfate particles in an aerosol to be introduced into the apparatus from 36, 37, 52, 61, 93, 137, to 199 μg/$m^3$. FIG. 14 shows a relationship between an accumulated mass of a microparticles introduced into the apparatus and a time integration amount of ion signals (sum of m/z 48 and m/z 64).

As a result, the accumulated mass of microparticles and the time integration amount of ion signals had a positive correlation, and satisfactory linearity was exhibited in the correlation therebetween in the range of the mass of microparticles subjected to the test. Thus, it was clarified that microparticles was able to be analyzed quantitatively.

Test Example 3

Measurement of Nitrate Aerosol and Analysis of Capture Efficiency of Microparticles The particle capture efficiency of a particle trap was analyzed. An aerosol containing potassium nitrate particles was measured in the same way as in Test Example 1.

It should be noted that, in order to measure the capture efficiency, it is necessary to grasp the state in which 100% of microparticles introduced into the apparatus and applied to the particle trap were measured. Then, potassium nitrate particles coated with oil (oleic acid) were generated and measured, and the result of the measurement was grasped. More specifically, it is known from the conventional study that, when dry solid particles such as potassium nitrate and ammonium sulfate collide with a surface at a high speed, a considerable part thereof bounces off the surface, but liquid particles such as oil or solid particles which are coated with a liquid to some degree hardly bounce off the surface. In other words, when the latter is measured, it may be considered that 100% of microparticles introduced into the apparatus and applied to the particle trap were measured.

Figure 15:
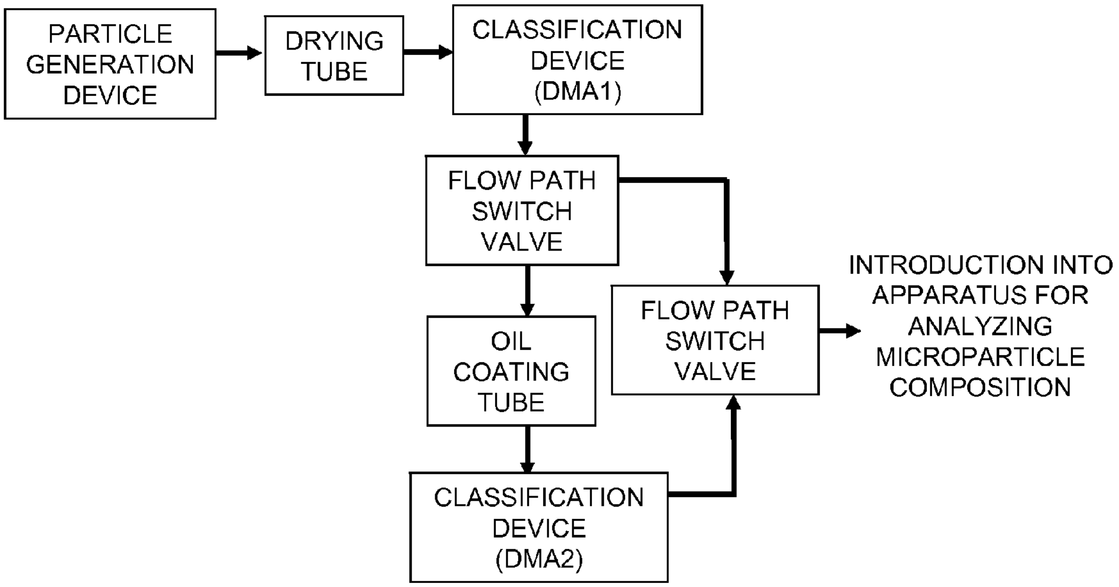
FIG. 15 A flowchart illustrating the steps of generating an aerosol containing monodisperse potassium nitrate particles coated with oil (oleic acid).

In view of the foregoing, with the flowchart illustrated in FIG. 15, a signal intensity for dry potassium nitrate particles and a signal intensity for the coated particles (in both cases, a signal intensity based on a unit mass of potassium nitrate) were measured and compared with each other to determine the capture efficiency of the dry potassium nitrate particles. More specifically, in a particle generation device, a potassium nitrate aqueous solution was sprayed and dried through a drying tube to generate polydisperse particles, and thereafter, the polydisperse particles were allowed to pass through a first classification device (DMA1) to obtain an aerosol containing monodisperse potassium nitrate particles. Further, the aerosol was allowed to pass through an oil coating tube by a branching flow path through a switch valve to be coated with oil (oleic acid), and the coated aerosol was further allowed to pass through a second classification device (DMA2) to obtain an aerosol containing monodisperse potassium nitrate particles coated with oil (oleic acid). The flow path of each of the aerosols was controlled with the switch valve so as to introduce the aerosol into the apparatus for analyzing a microparticle composition, and each of the aerosols was measured. The mass peak was measured at m/z 30 (signal of NO) and m/z 46 (signal of $NO_2$).

Figure 16:
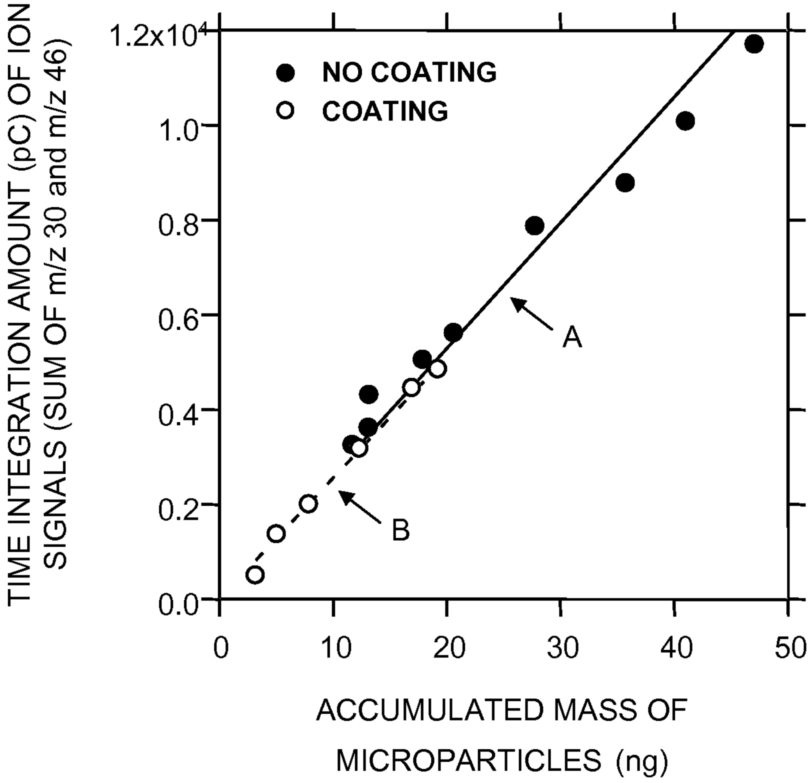
FIG. 16 A graph showing a positive correlation between an accumulated mass of microparticles and a time integration amount of ion signals for potassium nitrate particles.

As a result, as shown in FIG. 16, satisfactory measurement linearity was exhibited in both a regression line (straight line indicated by A in the figure) representing a correlation between the accumulated mass of microparticles and the time integration amount of ion signals for dry potassium nitrate particles and a regression line (straight line indicated by B in the figure) representing a correlation between the accumulated mass of microparticles and the time integration amount of ion signals for potassium nitrate particles coated with oil (oleic acid), and both the regression lines were overlapped on an extrapolation line thereof. With this, it was confirmed that the capture efficiency of the dry potassium nitrate particles was close to 100%, and it was clarified that the collection efficiency was enhanced remarkably compared with that of the conventional method of irradiating tungsten, molybdenum, or the like with a particle beam of microparticles, followed by measurement.

REFERENCE SIGNS LIST

1 aerodynamic lens
2 particle beam of microparticles
3 skimmer
4 skimmer portion
5 laser supply
5*a* laser
6*a*, 6*b* optical window
7 particle trap
7*a* particle trap supporting portion
8, 8*a*, 8*b* duct
9 ionization region
10 mass spectrometer

11*a*, 11*b*, 11*c* vacuum chamber
12 first partition
13 second partition
14*a*, 14*b*, 14*c* evacuation device
15 thermocouple temperature sensor
16 Peltier cooling element
17 particle trap holder
18 catalyst
19, 19*a*, 19*b* valve
20 housing
21*a*, 21*b*, 21*c*, 21*d* orifice
22 sample inlet
23 sample outlet
24 nozzle
40, 45 mesh-shaped structure
40*a*, 40*b*, 40*c*, 40*d* mesh layer
41 first mesh-shaped structure
41*a*, 41*b*, 41*c* grid layer
42 second mesh-shaped structure
43 plate having no void
50 apparatus for analyzing a microparticle composition
100, 100*a*, 100*b*, 100*c*, 100*d*, 100*e* mesh structure substrates
101 mesh
102 support frame
200 microfabricated compact

The invention claimed is:

1. A method of obtaining a component of a microparticle composition to be analyzed, using a particle trap having a mesh-shaped structure for capturing microparticles of the microparticle composition, the method comprising:
- converging microparticles in a gas sample to form a particle beam, wherein an excess gas phase component in the gas sample is removed from the particle beam;
- capturing the microparticles in the particle beam with the particle trap having the mesh-shaped structure by irradiating a narrow region of the particle trap with the particle beam; and
- vaporizing, sublimating, or reacting the microparticles captured by the particle trap by performing concentrated irradiation of the narrow region of the particle trap in which the microparticles are captured with an energy beam to yield a desorbed component for analysis;
- wherein the mesh-shaped structure of the particle trap comprises (i) a first mesh-shaped structure having a predetermined porosity and which is disposed on a front side of the particle trap, which front side is to be irradiated with the particle beam, and (ii) a second mesh-shaped structure having a porosity smaller than that of the first mesh-shaped structure, which is disposed on a back side of the particle trap which is a side opposite to the front side, the second mesh-shaped structure being connected to the first mesh-shaped structure.

2. The method according to claim 1, wherein the energy beam is selected or controlled depending upon energy absorption characteristics of constituent components of the microparticles.

3. The method according to claim 1, wherein the narrow region has a diameter of 1 mm to 3 mm.

4. The method according to claim 1, wherein the mesh-shaped structure is formed of a noble metal having a catalytic action.

5. The method according to claim 1, wherein the capturing of the microparticles with the particle trap is carried out while a temperature of the particle trap is controlled to be a temperature at which evaporation of a highly volatile component of the microparticles captured by the particle trap is reduced.

6. The method according to claim 1, wherein the desorbed component is converted into another substance through use of a catalyst, and the converted substance is analyzed.

7. A method of obtaining a component of a microparticle composition to be analyzed, using a particle trap having a mesh-shaped structure for capturing microparticles of the microparticle composition, the method comprising:
- converging microparticles in a gas sample to form a particle beam, wherein an excess gas phase component in the gas sample is removed from the particle beam;
- capturing the microparticles in the particle beam with the particle trap having the mesh-shaped structure by irradiating a narrow region of the particle trap with the particle beam; and
- vaporizing, sublimating, or reacting the microparticles captured by the particle trap by performing concentrated irradiation of the narrow region of the particle trap in which the microparticles are captured with an energy beam to yield a desorbed component for analysis;
- wherein the mesh-shaped structure of the particle trap comprises (i) a front-side mesh-shaped structure having a predetermined porosity and which is disposed on a front side of the particle trap, which front side is to be irradiated with the particle beam, and (ii) a plate having no void, which is disposed on a back side of the particle trap which is a side opposite to the front side, the plate being connected to the front-side mesh-shaped structure, and
- wherein the front-side mesh-shaped structure comprises a laminate of a plurality of mesh structure substrates formed of a mesh having a grid-like opening and a support frame for supporting an outer circumference of the mesh.

8. The method according to claim 7, wherein the energy beam is selected or controlled depending upon energy absorption characteristics of constituent components of the microparticles.

9. The method according to claim 7, wherein the narrow region has a diameter of 1 mm to 3 mm.

10. The method according to claim 7, wherein the mesh-shaped structure is formed of a noble metal having a catalytic action.

11. The method according to claim 7, wherein the capturing of the microparticles with the particle trap is carried out while a temperature of the particle trap is controlled to a temperature at which evaporation of a highly volatile component of the microparticles captured by the particle trap is reduced.

12. The method according to claim 7, wherein the desorbed component is converted into another substance through use of a catalyst, and the converted substance is analyzed.

* * * * *